(12) United States Patent
Ozeki et al.

(10) Patent No.: US 6,906,763 B2
(45) Date of Patent: Jun. 14, 2005

(54) LIQUID CRYSTAL DISPLAY DEVICE AND INSPECTION METHOD FOR A TRANSPARENT SUBSTRATE

(75) Inventors: Masao Ozeki, Kanagawa (JP); Werner Fertig, Babenhausen (DE); Christian Lauenstein, Babenhausen (DE)

(73) Assignees: OPTREX Corporation, Tokyo (JP); OPTREX EUROPE GmbH, Babenhausen (DE)

(*) Notice: Subject to any disclaimer, the term of this patent is extended or adjusted under 35 U.S.C. 154(b) by 67 days.

(21) Appl. No.: 10/423,940

(22) Filed: Apr. 28, 2003

(65) Prior Publication Data

US 2004/0008297 A1 Jan. 15, 2004

(30) Foreign Application Priority Data

Apr. 26, 2002 (JP) ........................................ 2002-126916

(51) Int. Cl.[7] ............................................ G02F 1/1347
(52) U.S. Cl. ............................... 349/75; 349/74; 349/76; 349/158
(58) Field of Search ........................... 349/74, 75, 76, 349/117, 158

(56) References Cited

U.S. PATENT DOCUMENTS

| | | | |
|---|---|---|---|
| 4,523,812 A | | 6/1985 | Penz |
| 5,757,447 A | * | 5/1998 | Kobayashi et al. ............ 349/70 |
| 5,760,859 A | * | 6/1998 | Bosma et al. ................. 349/75 |
| 5,841,492 A | * | 11/1998 | Iwauchi et al. ............... 349/74 |
| 5,953,090 A | | 9/1999 | Ozeki et al. |

| | | | |
|---|---|---|---|
| 2002/0030823 A1 | | 3/2002 | Kobayashi et al. |

FOREIGN PATENT DOCUMENTS

| | | |
|---|---|---|
| EP | 0 942 228 | 9/1999 |
| WO | WO 02/12825 | 2/2002 |

OTHER PUBLICATIONS

Patent Abstracts of Japan, JP 63–271423, Nov. 9, 1988.
M. Bosma, et al., SID International Symposium Digest of Technical Papers, vol. 28, XP–000722789, pp. 679–682, "LP–F: Late–News Poster: Twisted Liquid–Crystalline Retarders Providing Temperature–Matched Compensation of STN Displays", May 13, 1997.
Y. T. Mazurenko, et al., Optics Communications, vol. 133, No. 1–6, pp. 87–92, XP–002260377, "Spectral Coding for Secure Optical Communications Using Refractive Index Dispersion", Jan. 1, 1997.

* cited by examiner

*Primary Examiner*—Tarifur R. Chowdhury
*Assistant Examiner*—Michael H Caley
(74) *Attorney, Agent, or Firm*—Oblon, Spivak, McClelland, Maier & Neustadt, P.C.

(57) ABSTRACT

A liquid display device of D-STN mode capable of suppressing a line-shaped ununiformity of brightness in displaying a dark appearance is presented. A displaying cell 1 and a compensation cell 21 are formed so that there is a difference of thickness of at least 0.05 mm between the thickness of a glass substrate 2 at a front side of the displaying cell 1 and the thickness of a glass substrate at a rear side of the compensation cell 21. The displaying cell 1 and the compensation cell 21 are arranged between a first polarizing plate 32 and a second polarizing plate 33. A backlight 31 is of a type emitting light whose half value width with respect to the peak luminance is at least 5 nm.

6 Claims, 11 Drawing Sheets

Thickness of second glass substrate: 0.5 mm (500,000 nm)

Thickness of second glass substrate: 0.52 mm (520,000 nm)

Thickness of second glass substrate: 0.54 mm (540,000 nm)

Thickness of second glass substrate: 0.55 mm (550,000 nm)

Thickness of second glass substrate: 0.56 mm (560,000 nm)

Thickness of second glass substrate: 0.60 mm (600,000 nm)

Thickness of second glass substrate: 500,000nm

Thickness of first glass substrate: 500,000nm

Thickness of first glass substrate: 500,100nm

Thickness of second glass substrate: 500,000nm

Thickness of first glass substrate: 550,000nm

Thickness of first glass substrate: 550,100nm

Thickness of second glass substrate: 0.55 mm (550,000 nm)

Thickness of second glass substrate: 0.56 mm (560,000 nm)

Thickness of second glass substrate: 0.60 mm (600,000 nm)

LIQUID CRYSTAL DISPLAY DEVICE AND INSPECTION METHOD FOR A TRANSPARENT SUBSTRATE

BACKGROUND OF THE INVENTION

1. Field of the Invention

The present invention relates to a liquid crystal display device and an inspection method for a transparent substrate. The present invention relates, in particular, to a liquid crystal display device of D-STN (Double layered Super-Twisted Nematic) mode.

2. Discussion of Background

Various kinds of liquid crystal display device of TN (Twisted Nematic) mode, STN (Super-Twisted Nematic) mode or the like have widely been used. The liquid crystal display device of TN mode is of such a system that a nematic liquid crystal is sandwiched by two glass substrates wherein the direction of long axis of liquid crystal molecules is twisted 90° between the glass substrates. The device of STN mode is of a system that the twist angle is 180° or more in order to obtain a sharp change in the intensity of transmitting light to an applicable voltage.

When a monochrome display of a light source color and a dark appearance is to be performed in the STN mode, a retardation plate or a compensation cell is used in addition to a displaying liquid crystal cell. The system performing the monochrome display of a light source color and a dark appearance by using the compensation cell is referred to as D-STN mode. FIG. 19 is a diagrammatically cross-sectional view of a conventional liquid crystal display device of D-STN mode in the D-STN mode, a displaying cell 101 and a compensation cell 201 are provided between a first polarizing plate 302 and a second polarizing plate 303, and a backlight 301 is disposed at a rear surface side of the first polarizing plate 302. In the following, the side at which the backlight 301 is disposed is referred to as a rear surface side and the side at which the second polarizing plate 303 is disposed is referred to as a front surface side.

In the displaying cell 101, a liquid crystal layer 105 is sandwiched by a pair of glass substrates 102, 108 having transparent electrodes 103, 107. Alignment films 104, 106 are disposed on opposing surfaces of the transparent electrodes 103, 107.

In the compensation cell 201, a liquid crystal layer 205 is sandwiched by a pair of glass substrates 202, 208 having alignment films 204, 206. The liquid crystal layer 105 of the displaying cell 101 and the liquid crystal layer 205 of the compensation cell 201 have a relation that twist angles are the same and the direction of twisting of long axis of liquid crystal molecules in either cell is opposite to that of the other. Further, birefringence values of the two liquid crystal layers 105, 205 are equal. In addition, directions of alignment of liquid crystal molecules in the displaying cell 101 and the compensation cell 201 at sides of adjacent glass substrates are perpendicular to each other. Namely, the direction of alignment of liquid crystal molecules in the liquid crystal layer 105 of the displaying cell 101 at a side of glass substrate 102 is perpendicular to the direction of alignment of liquid crystal molecules in the liquid crystal layer 205 of the compensation cell 201 at a side of glass substrate 208.

The glass substrate 102 at a front surface side of the displaying cell 101 and the glass substrate 208 at a rear surface side of the compensation cell 201 are so designed as to have the same thickness.

If the distance (the air space) between the glass substrate 102 at a front surface side of the displaying cell 101 and the glass substrate 208 at a rear surface side of the compensation cell 201 is too small, interference fringes (Newton rings) are generated due to the air space. Accordingly, in the conventional technique, the thickness of the air space formed between the glass substrate 102 and the glass substrate 208 was determined to have a specified value. The first polarizing plate 302 is bonded to the glass substrate 108 at a rear surface side of the displaying cell 101, and the second polarizing plate 303 is also bonded to the glass substrate 202 at a front surface side of the compensation cell 201. The direction of polarization axis of the first polarizing plate 302 and the direction of polarization axis of the second polarizing plate 302 are perpendicular to each other. Further, it is preferable that a direction of polarization axis of the first polarizing plate 302 and the direction of alignment of liquid crystal molecules in the liquid crystal layer 105 of the displaying cell 101 at a side of glass substrate 108 (a rear surface side) form an angle of 45°, and the direction of polarization axis of the second polarizing plate 303 and the direction of alignment of liquid crystal molecules in the liquid crystal layer 205 of the compensation cell at a side of glass substrate 202 (a front surface side) form an angle of 45°, in order to obtain a display of good light source color.

When a dark appearance is to be displayed, no voltage is applied to the liquid crystal layer 105 of the displaying cell 101, or a voltage lower than the predetermined threshold voltage is applied. A first path 351 shown in FIG. 19 indicates the path of light when the dark appearance is to be displayed. Light from the backlight 301 presents a linearly polarized light after it has passed through the first polarizing plate 302. Further, after passing through the displaying cell 101, it presents an elliptically polarized light. However, the light is again rendered to be a linearly polarized light by means of the compensation cell 201. As a result, the light is interrupted by the second polarizing plate 303 as shown by the first path 351 whereby the liquid crystal display device presents the dark appearance. When the light source color is to be displayed, the state of alignment of liquid crystal molecules is changed by applying a voltage to the liquid crystal layer 105 of the displaying cell 101.

Even in a case that a retardation plate is disposed in place of the compensation cell 201, the same display as in the D-STN mode can be realized. However, the quality of display in using the retardation plate is apt to suffer influence due to a temperature change. Accordingly, the D-STN mode is often used in, for example, an in-vehicle liquid crystal display device having a wide range of temperature change in environment of use.

SUMMARY OF THE INVENTION

In the conventional liquid crystal display device of D-STN mode, when a dark appearance was to be displayed by blocking light from the backlight 301, there was a case causing leakage of light from the second polarizing plate 303 whereby a line-shaped ununiformity of brightness as exemplified in FIG. 20 might generate in the display of the dark appearance. Such leakage of light was particularly remarkable in a liquid crystal display device using a backlight having a specified wavelength (e.g., a wavelength of red color). Accordingly, there has been expected to overcome such problem of the line-shaped ununiformity of brightness to improve yield in the production of the liquid crystal display device of D-STN mode. However, the improvement of yield was difficult because the cause of the generation of the line-shaped ununiformity of brightness in the display screen due to the leakage of light was unclear.

Further, in the production of a transparent substrate such as a glass substrate or the like, it is preferred that it is possible to confirm easily unevenness in the thickness of the transparent substrate.

It is an object of the present invention to provide a liquid crystal display device of D-STN mode presenting a display of good dark appearance without generating a line-shaped ununiformity of brightness.

Further, it is an object of the present invention to provide an inspection method for a transparent substrate, capable of confirming easily unevenness in the thickness of a transparent substrate.

The inventors of this application have studied the cause of leakage of light when a dark appearance is to be displayed. As a result, they have found the cause of leakage of light and the cause of the line-shaped ununiformity of brightness. FIG. 21 is a diagram showing the cause of leakage of light. A second path 352 shown in FIG. 21 indicates an example of a path of light passing through the second polarizing plate 303. Light from the backlight 301 does not always trace the first path 351 as shown in FIG. 19, but a part of light from the backlight 301 is reflected in the displaying cell 101. For example, a part of light, as shown by the second path 352, which has passed through the liquid crystal layer 105 of the displaying cell 101 reflects at the glass substrate 102 located at a front surface side of the displaying cell 101, passes again through the liquid crystal layer 105, reflects at a transparent electrode 107 located at a rear surface side of the displaying cell 101 and passes again through the liquid crystal layer 105. In this case, the light passes through the liquid crystal layer 105 three times, and also passes through the glass substrate 102 at a front surface side of the displaying cell 101 three times.

When light which has passed more than three times through the liquid crystal layer 105 due to internal reflection in the displaying cell 101 reaches a compensation cell 201 after having passed through the glass substrate 102 at a front surface side of the displaying cell 101, the compensation cell 201 cannot perform the complete compensation to the light. Namely, it is impossible to transform the light passing through the displaying cell 101, by which an elliptically polarized light is presented, into a linearly polarized light completely. As a result, the light internally reflected passes through a second polarizing plate 303.

Further, when the light having passed more than three times through the liquid crystal layer 105 reaches the compensation cell 201, the light may cause internal reflection at a glass substrate 208 located at a rear surface side of the compensation cell 201. In this case, the light passes three times through the glass substrate 102 at a front surface side of the displaying cell 101 and the glass substrate 208 at a rear surface side of the compensation cell 201 as indicated by the second path 352. Then, interference of light is caused as a result that the light passes plural times through glass substrates 102, 208 adjacent to each other. Although the glass substrate 102 and the glass substrate 208 are so designed as to have the same thickness, there results, in fact, unevenness in the thickness of the glass substrates during production. For example, when a glass substrate having a size of 5 cm×5 cm is produced, it is presumed that a difference of thickness of from 1 to 2 $\mu$m is resulted between the thickest portion and the thinnest portion. Accordingly, when the glass substrate 208 and the glass substrate 102 do not have uniform thicknesses, there appear a strong portion and a weak portion of interference of light caused by the adjacent glass substrates 102, 208, whereby a line-shaped ununiformity of brightness as shown in FIG. 20 is recognized. Such line-shaped ununiformity of brightness is different from Newton rings.

As the size of a glass substrate is larger, the degree of unevenness in the thickness of the glass substrate produced becomes larger. For example, when a glass substrate having a size of 30 cm×40 cm is produced, there causes a difference of thickness of about 10 $\mu$m between the thickest portion and the thinnest portion.

There is a case that the internally reflected light traces a path other than the second path 352. For example, there is a case that light reaches the compensation cell 201 after having passed 5 times or 7 times through the liquid crystal layer 105 by internal reflection in the displaying cell 101. However, when the light passes through the liquid crystal layer 105 5 times or 7 times, the quantity of the light attenuates. Accordingly, light which has passed three times through the liquid crystal layer 105 in the internally reflected light gives a dominant influence to the quality of a display of dark appearance. Here, description has been made as to the light internally reflected in the displaying cell. However, the internal reflection is generated in the compensation cell as well, and light internally reflected in the compensation cell 201 may pass through the second polarizing plate 303.

The inventors of this application have achieved the present invention described hereinbelow, based on the above-mentioned findings.

According to a first aspect of the present invention, there is provided a liquid crystal display device comprising:

a displaying liquid crystal cell having a liquid crystal layer sandwiched by a pair of transparent substrates with transparent electrodes so as to maintain a state of twisted alignment when a voltage applied to the liquid crystal layer is not more than the threshold voltage, a compensation cell having a liquid crystal layer sandwiched by a pair of transparent substrates so as to maintain a state of twisted alignment in which the direction of twisting is opposite to that in the displaying liquid crystal cell and the twist angle is substantially the same as that of the displaying liquid crystal, the compensation cell having substantially the same retardation value as the displaying liquid crystal cell, wherein the displaying liquid crystal cell and the compensation cell are arranged so that directions of alignment of liquid crystal molecules at sides of adjacent transparent substrates are substantially perpendicular to each other, and a pair of polarizing plates disposed to sandwich the displaying liquid crystal cell and the compensation cell so that their polarization axes are substantially perpendicular to each other, the liquid crystal display device being characterized in that:

a backlight is disposed to irradiate light whose half value width with respect to the peak luminance is at least 5 nm, and there is a difference of thickness of at least 0.05 mm between the thickness of the transparent substrate of the displaying liquid crystal cell at a side of compensation cell and the thickness of the transparent substrate of the compensation cell at a side of displaying liquid crystal cell.

According to a second aspect of the present invention, there is provided the liquid crystal display device as described above, wherein the liquid crystal display device is an in-vehicle liquid crystal display device mounted on a vehicle or a displaying liquid crystal device for presenting information to public.

According to a third aspect of the present invention, there is provided the liquid crystal display device as described above, wherein there is an air space of at least 75 μm between the displaying liquid crystal cell and the compensation cell.

According to a fourth aspect of the present invention, there is provided a liquid display device comprising:

a displaying liquid crystal cell having a liquid crystal layer sandwiched by a pair of transparent substrates with transparent electrodes so as to maintain a state of twisted alignment when a voltage applied to the liquid crystal layer is not more than the threshold voltage, a compensation cell having a liquid crystal layer sandwiched by a pair of transparent substrates so as to maintain a state of twisted alignment in which the direction of twisting is opposite to that in the displaying liquid crystal cell and the twist angle is substantially the same as that of the displaying liquid crystal cell, the compensation cell having substantially the same retardation value as the displaying liquid crystal, wherein the displaying liquid crystal cell and the compensation cell are arranged so that directions of alignment of liquid crystal molecules at sides of adjacent transparent substrates are substantially perpendicular to each other, and a pair of polarizing plates arranged to sandwich the displaying liquid crystal cell and the compensation cell so that their polarization axes are substantially perpendicular to each other, the liquid crystal display device being characterized in that:

a backlight is disposed to irradiate light whose half value width with respect to the peak luminance is at least 5 nm, and the transparent substrate of the displaying liquid crystal cell at a side of compensation cell and the transparent substrate of the compensation cell at a side of displaying liquid crystal cell are provided with first transparent sheets of substantially same thickness, and the first transparent sheet of either the transparent substrate of the displaying liquid crystal cell at a side of compensation cell or the transparent substrate of the compensation cell at a side of displaying liquid crystal cell is in optically close contact with a second transparent sheet having a thickness of at least 0.05 mm.

According to a fifth aspect of the present invention, there is provided an inspection method for inspecting a distribution of thickness of a transparent substrate, characterized in that:

a first transparent substrate having a known distribution of thickness and a second transparent substrate to be inspected are prepared, wherein the difference of thickness in average between first and second transparent substrates is not more than 50 μm, the first transparent substrate and the second transparent substrate are arranged so that light transmits through a first substrate and a second substrate, a substrate gap of at least 0.1 mm is provided between the first substrate and the second substrate, a light source for irradiating light whose halt value width with respect to the peak luminance is at least 5 nm is prepared, and the degree of distribution of thickness of the second transparent substrate is judged from an interference intensity distribution of light passing through the first transparent substrate and the second transparent substrate.

According to a sixth aspect of the present invention, there is provided the inspection method for a transparent substrate as described just above, wherein the judgment to the interference intensity distribution generated in the second transparent substrate is made according to the number of interference fringes generated by interference of light passing through the first transparent substrate and the second transparent substrate.

DETAILED DESCRIPTION OF THE PREFERRED EMBODIMENTS

Figure 1:
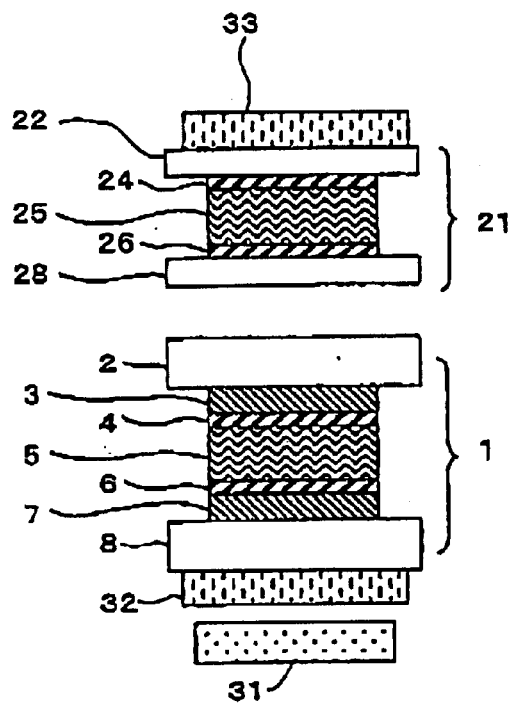
FIG. 1 is a diagrammatic cross-sectional view showing an embodiment of the liquid crystal display device according to the present invention.

In the following, preferred embodiments of the present invention will be described with reference to the drawing.

FIG. 1 is a diagrammatic cross-sectional view of the liquid crystal display device according to an embodiment of the present invention. The liquid crystal display device is of a D-STN mode and is provided with a first polarizing plate 32, a second polarizing plate 33, a displaying cell (a displaying liquid crystal cell) 1 sandwiched between the first and second polarizing plates 32, 33, and a compensation cell 21. A backlight 31 is located at a rear surface side of the first polarizing plate 32 so as to emit light having a half value width of at least 5 nm with respect to the peak luminance (a width of wavelength at a half luminance of the peak luminance). In the following description, a side at which the backlight 31 is disposed is referred to as a rear surface side, and a side at which the second polarizing plate 33 is disposed is referred to as a front surface side.

In the displaying cell 1, a liquid crystal layer 5 is sandwiched by a glass substrate (a transparent substrate) 2, located at a front surface side, on which a transparent electrode 3 is formed and a glass substrate (a transparent substrate), at a front surface side, on which a transparent electrode 7 is formed. The transparent electrodes 3, 7 opposing by interposing the liquid crystal layer 5 therebetween are provided with alignment films 4, 6 on their opposing surfaces. The alignment films 4, 6 are subjected to a rubbing treatment. When a voltage applied to the liquid crystal layer 5 is not more than a predetermined threshold voltage, the displaying cell 1 maintains a state of twisted alignment in the liquid crystal layer 5 by the presence of the alignment films 4, 6. In the compensation cell 21, a liquid crystal layer 25 is sandwiched by a glass substrate (a transparent substrate) 22, at a front surface side, on which an alignment film 24 is formed and a glass substrate (a transparent substrate) 28, at a rear surface side, on which an alignment film 26 is formed. The alignment films 24, 26 of the compensation cell 21 are also subjected to a rubbing treatment. The compensation cell 21 maintains a state of twisted alignment of the liquid crystal layer 25 by the presence of the alignment films 24, 26.

There is a difference of at least 0.05 mm between the thickness of the glass substrate 2 and the thickness of the glass substrate 28 which are in the displaying 1 and the compensation cell 21 and are adjacent to each other. Namely, there is a difference of at least 0.05 mm (50 $\mu$m) between the thickness of the glass substrate 2 located at a front surface side (a side of compensation cell) of the displaying cell 1 and the thickness of the glass substrate 28 located at a rear surface side (a side of displaying cell) of the compensation cell 21. FIG. 1 shows a case that the glass substrate 2 at a front surface side of the displaying cell 1 is at least 0.05 mm thicker than the glass substrate 28 at a rear surface side of the compensation cell 21. The thickness of the glass substrate 8 at a rear surface side of the displaying cell 1 is made equal to the thickness of the glass substrate 2 at a front surface side of the displaying cell 1, in this embodiment. The thickness of the glass substrate 22 at a front surface side of the compensation cell 21 is equal to the thickness of the glass substrate 28 at a rear surface side of the compensation cell 21, in this embodiment. However, thicknesses of glass substrates 2, 8 of the displaying cell 1 may not be equal. Similarly, thicknesses of the glass substrates 22, 28 of the compensation cell 21 may not be equal.

When each glass substrate 2, 8, 22 or 28 is produced, unevenness of thickness may takes place in each glass substrate. It is permissible that unevenness of thickness takes place in each of the glass substrates 2, 8, 22 and 28 as far as it is not beyond the normal range of unevenness in producing glass substrates. For example, it is assumed that a glass substrate having a size of 5 cm×5 cm and a thickness of 0.55 mm is produced as the glass substrate 2. In this case, a difference of thickness of, for example, 2 $\mu$m between the thickest portion and the thinnest portion is permissible. The same condition is applicable to other glass substrates 8, 22 and 28.

The liquid crystal layer 5 of the displaying cell 1 and the liquid crystal layer 25 of the compensation cell 21 have the same birefringence value. Further, the liquid crystal layer 5 of the displaying cell 1 and the liquid crystal layer 25 of the compensation cell 21 have such relation that when a voltage applied to the liquid crystal layer 5 is not more than the threshold voltage, they have the same twist angle and the direction of twisting of long axis of liquid crystal molecules of either cell is opposite to that of the other. In this case, directions of aligning of liquid crystal molecules of the displaying cell 1 and the compensation cell 21 at sides of adjacent glass substrates 2, 28 are perpendicular to each other. Namely, the direction in alignment in the liquid crystal layer 5 of the displaying cell at a side of glass substrate 2 is perpendicular to the direction of alignment in the liquid crystal layer 25 of the compensation cell 21 at a side of glass substrate 28. Further, the retardation value $\Delta n \cdot d$ of the displaying cell 1 is equal to the retardation value $\Delta n \cdot d$ of the compensation cell 21.

An air gap (an air space) of at least 75 $\mu$m is provided between the glass substrate 2 at a front surface side of the displaying cell 1 and the glass substrate 28 at a rear surface side of the compensation cell 21. The provision of the air space prevents interference caused by reflection of light at the surface of the glass substrate 2 at a front surface side of the displaying cell 1 and the surface of the glass substrate 28 at a rear side of the compensation cell 21. The first polarizing plate 32 is bonded to the glass substrate 8 at a rear surface side of the displaying cell 1. Similarly, the second polarizing plate 33 is bonded to the glass substrate 22 at a front surface side of the compensation cell 21. The direction of polarization axis of the first polarizing plate 32 and the direction of polarization axis of the second polarizing plate 33 are perpendicular to each other. Further, it is preferable that the direction of polarization axis of the first polarizing plate 32 and the direction of alignment of the liquid crystal layer 5 of the displaying cell 1 at a side of glass substrate 8 (a rear surface side) form an angle of 45°, and the direction of polarization axis of the second polarizing plate 33 and the direction of alignment of the liquid crystal layer 25 of the compensation cell 21 at a side of glass substrate 22 (a front surface side) form an angle of 45°. Thus, by specifying directions of polarization axes and directions of alignment, an excellent light source color can be obtained when a display of light source color is to be presented.

A display of dark appearance is expected, no voltage is applied to the liquid crystal layer 5 of the displaying cell 1 or a voltage of not more than the threshold voltage is applied to. In this case, light emitted from the backlight 31 is rendered to be a linearly polarized light when it is passed through the first polarizing plate 32, and it is rendered to be an elliptically polarized light when passed through the displaying cell 1. Then, the light is returned again to the linearly polarized light by the compensation cell 21 and is blocked by the second polarizing plate 33. Since there is internal reflection of a part of light emitted from the backlight 31 in the displaying cell or the compensation cell 21, light may leak from the second polarizing plate 33. However, there occurs only slight unevenness in the intensity of light passing through the glass substrates 2, 28 even though there is unevenness in the thickness of the glass substrate 2 at a front surface side of the displaying cell 1 or in the thickness of the glass substrate 28 at a rear surface side of the compensation cell 21, as described after. Accordingly, an excellent dark appearance can be presented without a line-shaped ununiformity of brightness.

When a light source color is to be displayed, a higher voltage than the threshold voltage should be applied to the liquid crystal layer 5 of the displaying cell 1 so that the long axis of each liquid crystal molecule in the liquid crystal layer 5 is aligned to the direction of the electric field.

The inventors of this application have studied in detail about a change of relative interference intensity in a glass substrate due to unevenness of the thickness of the glass substrate. As a result, it has been found that influence caused by an uneven thickness can be eliminated by providing a difference of thickness of at least 0.05 mm between adjacent glass substrates in the displaying cell and the compensation cell (more specifically, the glass substrate 2 at a front surface side of the displaying cell 1 and the glass substrate 28 at a rear surface side of the compensation cell 21 as shown in FIG. 1), and by irradiating light whose half value width with respect to the peak luminance of light from the backlight is at least 5 nm.

In the following, description will be made as to how unevenness in the thickness of a glass substrate affects the intensity of light passing through the glass plate.

A degree of interfering light affecting the intensity of light passing through a substrate is mentioned as an interference intensity. In general, an interference intensity in relative sense (a relative interference intensity) of a single glass substrate is expressed by the following formula 1:

$$P=1-\cos((A \times B \times 2/\lambda) \times 2 \times \pi) \quad \text{Formula 1}$$

In formula 1, a character A denotes a thickness of a glass substrate in a unit of nm, a character B denotes a refractive index of glass of the glass substrate and $\lambda$ denotes a wavelength of light in a unit of nm. A relative interference intensity given by two adjacent glass substrates is expressed as the product of relative interference intensities of the glass substrates. Accordingly, when a thickness of a second glass substrate is expressed by A' (nm) and a refractive index of glass is expressed by B', the relative interference intensity P with respect to a wavelength $\lambda$ (nm) is expressed by the following formula 2:

$$P=(1-\cos((A \times B \times 2/\lambda) \times 2 \times \pi)) \ast (1-\cos((A' \times B' \times 2/\lambda) \times 2 \times \pi)) \quad \text{Formula 2}$$

The relative interference intensity obtained by two glass substrates was calculated by using formula 2. The thickness of a first glass substrate was changed from 500,000 nm to 500,420 nm while the thickness of a second glass substrate was kept constant to 500,000 nm. Further, light having a half value width of 15 nm (with respect to the peak luminance (a width of ±7.5 nm with respect to the wavelength at the peak luminance) was supposed to be irradiated. By using LED, the light having a half value width of 15 nm is irradiated. A red-color light having a central wavelength of 640 nm is assumed.

Figure 2:
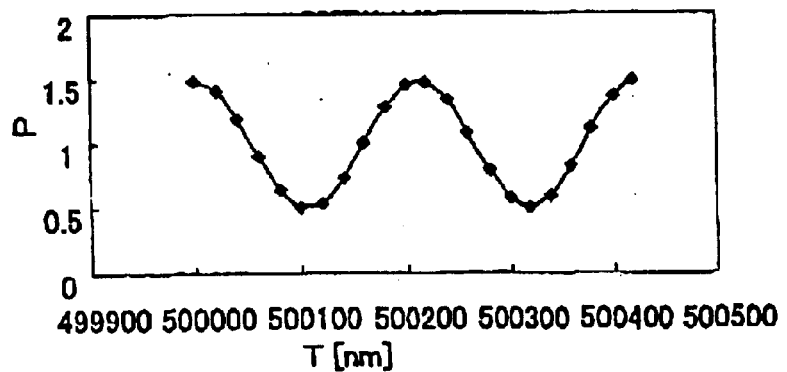
FIG. 2 is a graph showing a change of relative interference intensity caused by two glass substrates.

FIG. 2 shows a change of the relative interference intensity obtained by the combination of two glass substrates wherein the abscissa represents the thickness T of the first glass substrate and the ordinate represents the relative interference intensity P. As shown in FIG. 2, the relative interference intensity by the combination of the two glass substrates varies within a range of from about 1.5 to about 0.5 with a change of the thickness of the first glass substrate. For example, when the thickness of the first glass substrate is 500,000 nm, the relative interference intensity is about 1.5. However, when the thickness is 500,100 nm, the relative interference intensity is about 0.5. This shows that when unevenness of thickness results in either glass substrate, ununiformity of strength results also in the relative interference intensity.

Figure 3:
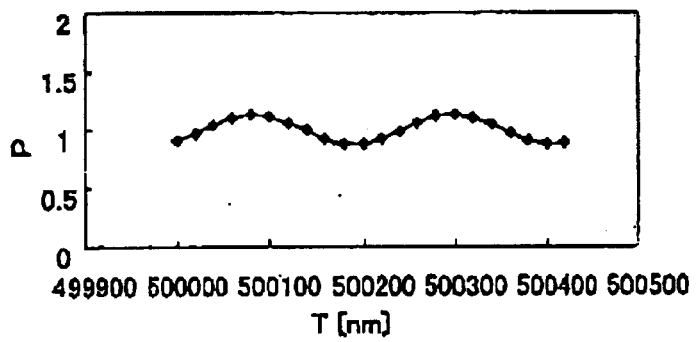
FIG. 3 is a graph showing a change of relative interference intensity caused by two glass substrates.

FIG. 3 is a graph showing a change of the relative interference intensity in a case that the thickness of the second glass substrate is determined to be 520,000 nm, in the same manner as in FIG. 2. Even in the case of FIG. 3, the relative interference intensity by the combination of two glass substrates varies with a change of the thickness of the first glass substrate. However, the difference between maximum and minimum values of the relative interference intensity is smaller than that in FIG. 2.

Figure 4:
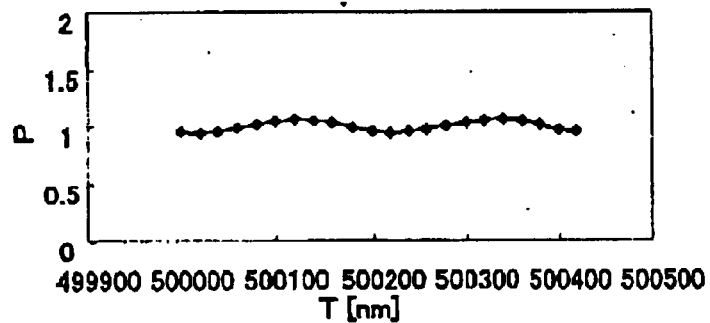
FIG. 4 is a graph showing a change of relative interference intensity caused by two glass substrates.

FIG. 4 is a graph showing a change of the relative interference intensity in a case that the thickness of the second glass substrate is determined to be 540,000 nm, in the same manner as in FIGS. 2 and 3. Even in the case of FIG. 4, the relative interference intensity by the combination of two glass substrates varies with a change of the thickness of the first glass substrate. However, the difference between the maximum and minimum values of the relative interference intensity is further smaller than that shown in FIG. 3.

Figure 5:
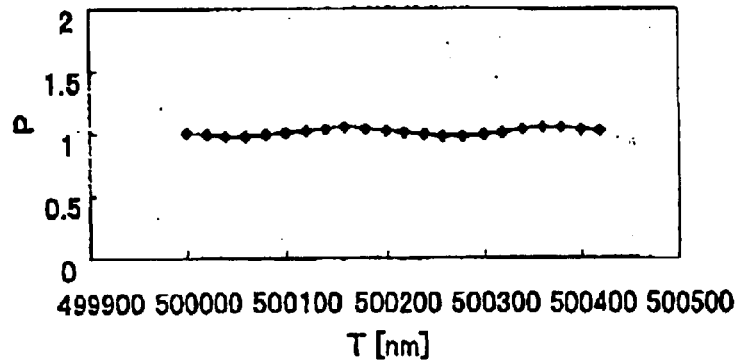
FIG. 5 is a graph showing a change of relative interference intensity caused by two glass substrates.
Figure 6:
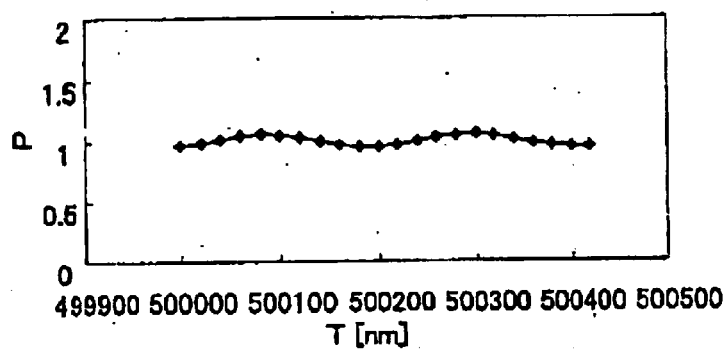
FIG. 6 is a graph showing a change of relative interference intensity caused by two glass substrates.
Figure 7:
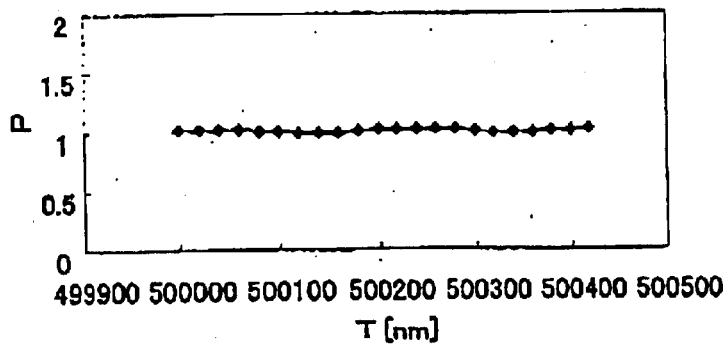
FIG. 7 is a graph showing a change of relative interference intensity caused by two glass substrates.

FIGS. 5, 6 and 7 show graphs showing changes of relative interference intensities in cases that the thickness of the second glass substrate are to be 550,000 nm, 560,000 nm and 600,000 nm, in the same manner as FIGS. 2 to 4. In the cases of FIGS. 5, 6 and 7, the relative interference intensities do not show substantial changes even when thickness of the first glass substrate are changed from 500,000 nm to 500,420 nm.

It is derived from FIGS. 2 to 7 that when the difference of thickness between adjacent glass substrates is smaller than 50,000 nm (0.05 mm) and if there is unevenness in the thickness of a glass substrate, the relative interference intensities are also changed. Further, it is derived that when the difference of thickness between adjacent glass substrates is at least 50000 nm (0.05 mm), the relative interference intensities do not show substantial changes even though there is unevenness in the thickness of a glass substrate. Thus, when the relative interference intensity does not show a substantial change even though there is unevenness in the thickness, the intensity of light leaking from the second polarizing plate 33 shown in FIG. 1 does not show a substantial change over the entire surface of it to thereby prevent the occurrence of a line-shaped uniformity of brightness. Accordingly, it is understood that the difference of thickness between adjacent glass substrates should be at least 0.05 mm in order to prevent the occurrence of a line-shaped ununiformity of brightness. Namely, in the liquid crystal display device shown in FIG. 1, it is necessary that the difference between the thickness of the glass substrate 2 at a front surface side of the displaying cell 1 and the thickness of the glass substrate 28 at a rear surface side of the compensation cell 21 is at least 0.05 mm.

Next, explanation will be made as to the reason why the change of the relative interference intensity caused by the unevenness of thickness can be suppressed by providing a difference of thickness between adjacent glass substrates.

Figure 8A:
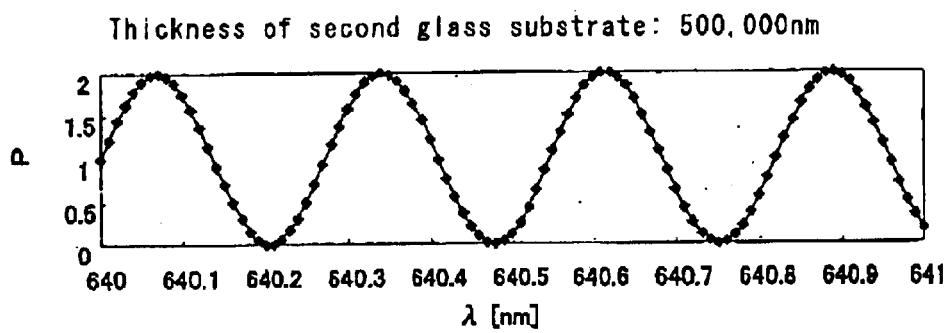
FIG. 8 is a graph showing a relative interference intensity of each glass substrate when thicknesses of adjacent glass substrates are both 0.5 mm.
Figure 8B:
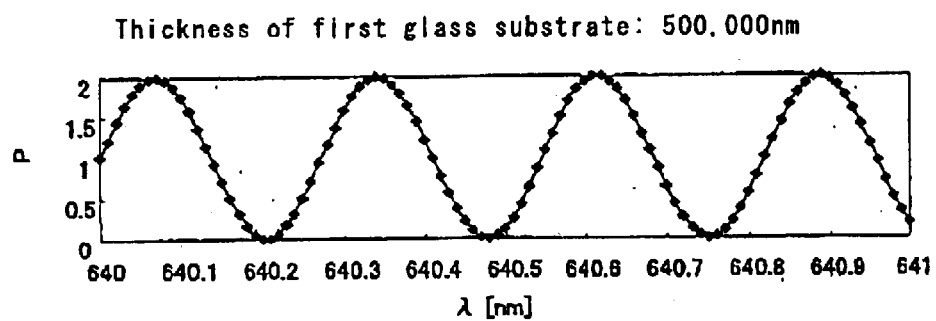
Figure 8C:
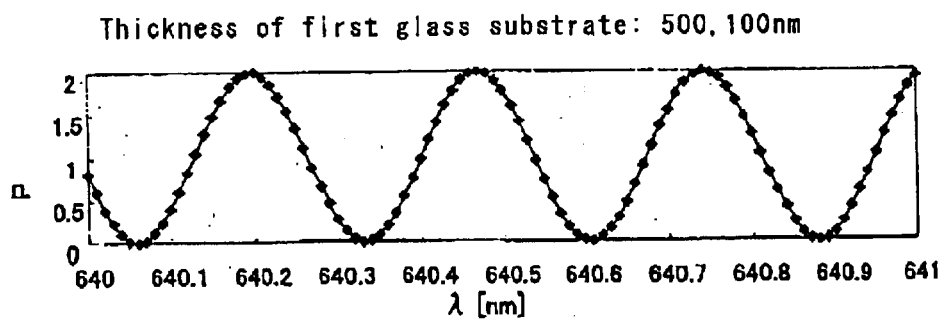

FIG. 8 is graphs showing the relative interference intensity of each glass substrate in a case that thicknesses of adjacent glass substrates are to be 500,000 nm (0.5 mm). The abscissa in FIGS. 8(a) to 8(c) denotes a wavelength $\lambda$ of light. The ordinate in FIG. 8(a) denotes the relative interference intensity of the second glass substrate having a thickness of 500,000 nm. The ordinate in FIG. 8(b) denotes the relative interference intensity of the first glass substrate having a thickness of 500,000 nm. The ordinate in FIG. 8(c) denotes the relative interference intensity of the first glass substrate having a thickness of 500,100 nm because of unevenness in the thickness.

As shown in FIGS. 8(a) to 8(c), relative interference intensities change periodically as the wavelength λ of light is changed. The change of the relative interference intensity shown in FIG. 8(b) is the same as the change of the relative interference intensity in FIG. 8(a) because this change is the same as the case that the second glass substrate has the same thickness. On the other hand, FIG. 8(c) shows a change of the relative interference intensity when there is a change of 100 nm in the thickness due to unevenness. The period of the change of the relative interference intensity is the same as that shown in FIG. 8(a) (although they are not the same in the strict sense, the difference of periods is negligible). Further, the phase of the waveform shown in FIG. 8(c) is delayed by about ½ with respect to the waveform shown in FIG. 8(a).

The relative interference intensity of two glass substrates can be expressed as the product of the relative interference intensities of the glass substrates. Accordingly, the relative interference intensity of light having a width in its wavelength λ passing through two glass substrates each having a thickness of 500,000 nm can be expressed as a value obtained by multiplying each relative interference intensity of the waveform shown in FIG. 8(a) by each relative interference intensity of the waveform shown in FIG. 8(b) for each wavelength λ and averaging the obtained values. Waveforms showing changes of the relative interference intensities in FIGS. 8(a) and 8(b) are the same. Accordingly, when the relative interference intensity of either one becomes larger, the relative interference intensity of the other becomes also larger. When the relative interference intensity of either-waveform becomes smaller, the relative interference intensity of the other becomes also smaller. For example, when λ is about 640.07 nm, relative interference intensities shown in FIGS. 8(a) and 8(b) become about 2. Further, when λ is about 640.2 nm for example, relative interference intensities shown in FIGS. 8(a) and 8(b) become about 0.

Assuming that there is unevenness in the thickness of the first glass substrate so that the glass substrate has a portion having a thickness of 500,100 nm. The relative interference intensity of light passing through this portion and the second glass substrate can be expressed as a value which is obtained by multiplying each relative interference intensity of the waveform shown in FIG. 8(a) by each relative interference intensity shown in FIG. 8(c), and by averaging the obtained products. Waveforms shown in FIGS. 8(a) and 8(c) have the same period and the phase of waveform of either one is delayed by about ½ from the other. Accordingly, when the relative interference intensity of either one becomes larger, the relative interference intensity of the other becomes smaller. For example, when λ is about 640.07 nm, the relative interference intensity in FIG. 8(a) is 2 whereas the relative interference intensity in FIG. 8(c) is about 0.

As described above, the waveforms shown in FIGS. 8(a) and 8(b) have such relation that when the relative interference intensity of either one becomes larger, the relative interference intensity of the other becomes also large, and when the relative interference intensity of either one becomes smaller, the relative interference intensity of the other becomes also smaller. Further, the waveforms shown in FIGS. 8(a) and 8(c) have such relation that when either one becomes larger, the other becomes smaller. In this case, there is a difference between a value obtained by multiplying each relative interference intensity of waveforms shown in FIGS. 8(a) and 8(b) for each wavelength λ, and summing the obtained products for each λ, and a value obtained by multiplying each relative interference intensity of waveforms shown in FIGS. 8(a) and 8(c) for each wavelength λ and summing the obtained products for each λ. This difference appears as a difference of relative interference intensities in the case there is unevenness in the thickness.

Figure 9A:
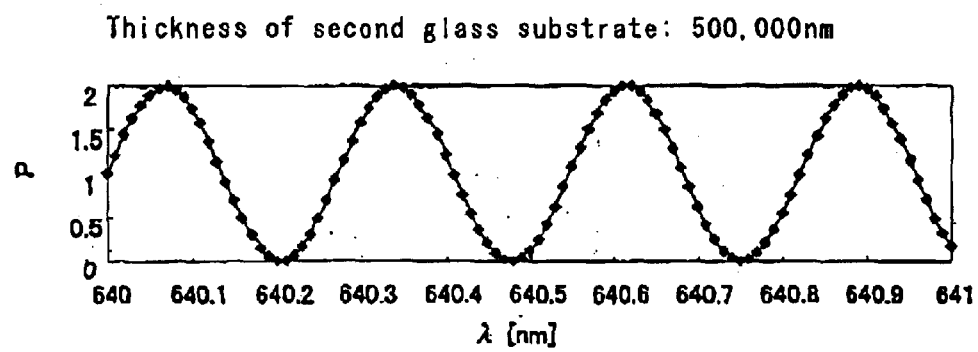
FIG. 9 is a graph showing a relative interference intensity of each glass substrate when thicknesses of adjacent glass substrates are 0.5 mm and 0.55 mm.
Figure 9B:
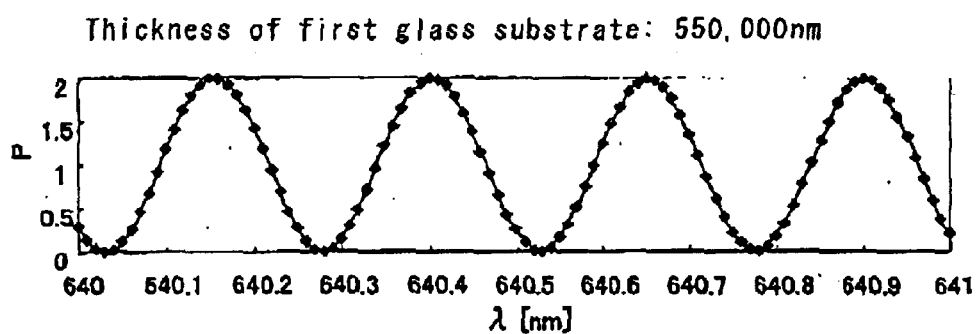
Figure 9C:
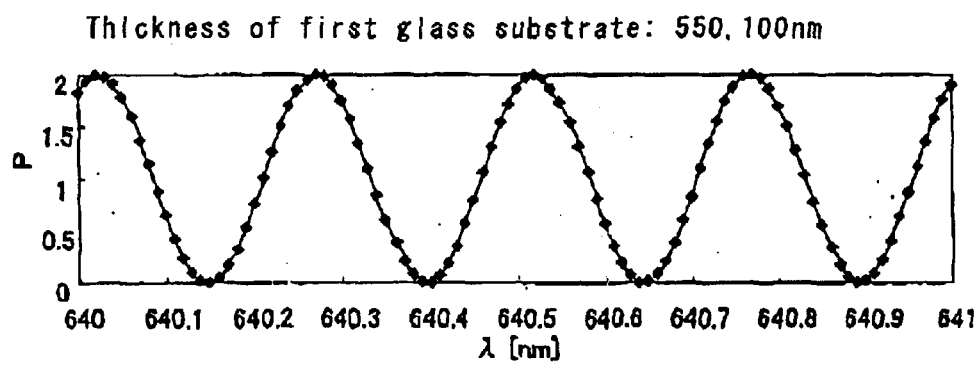

FIG. 9 shows the relative interference intensity of each glass substrate in a case that the thickness of either of adjacent glass substrates is 550,000 nm and the thickness of the other is 500,000 nm. The abscissa in FIGS. 9(a) to 9(c) denotes the wavelength λ of light. The ordinate in FIG. 9(a) denotes the relative interference intensity of the second glass substrate having a thickness of 500,000 nm, the ordinate in FIG. 9(b) denotes the relative interference intensity of the first glass substrate having a thickness of 550,000 nm, and the ordinate in FIG. 9(c) denotes the relative interference intensity of the first glass substrate having a thickness of 550,100 nm due to unevenness in the thickness.

As shown in FIGS. 9(a) to 9(c), relative interference intensities change periodically as the wavelength λ of light is changed. The period of the waveform shown in FIG. 9(a) is different from those of the waveforms shown in FIGS. 9(b) and 9(c). The waveforms shown in FIGS. 9(b) and 9(c) have the same period (although they are not the same in the strict sense, the difference of periods is negligible). However, there is a delay of phase of about ½ between them.

The relative interference intensity of light having a width in its wavelength passing through a glass substrate having a thickness of 550,000 nm and a glass substrate having a thickness of 500,000 nm can be expressed as a value obtained by multiplying each relative interference intensity of the waveform shown in FIG. 9(a) by each relative interference intensity of the waveform shown in FIG. 9(b) for each wavelength λ, and by averaging the obtained products. Waveforms shown in FIGS. 9(a) and 9(b) are different from each other in terms of period. Accordingly, such relation that when the relative interference intensity of either one becomes larger, the relative interference intensity of the other becomes also larger or such relation that when the relative interference intensity of either one becomes larger, the relative interference intensity of the other becomes smaller, cannot be maintained. For example, when λ is about 640.07 in FIGS. 9(a) and 9(b), the relative interference intensity in FIG. 9(a) is about 2, whereas the relative interference intensity in FIG. 9(b) is about 0.2. On the other hand, when λ is about 640.9, relative interference intensities in FIGS. 9(a) and 9(b) are about 2.

Assuming that there is unevenness in the thickness of the first glass substrate so that it has a portion having a thickness of 550,100 nm. The relative interference intensity of light passing through this portion and the second glass substrate can be expressed as a value obtained by multiplying each relative interference intensity of the waveform shown in FIG. 9(a) by each relative interference intensity of the waveform shown in FIG. 9(c) for each wavelength λ, and averaging the obtained products. Waveforms shown in FIGS. 9(a) and 9(c) are also different from each other in terms of period. Accordingly, such relation that when the relative interference intensity of either one becomes larger, the relative interference intensity of the other becomes also larger or such relation that when the relative interference intensity of either one becomes larger, the relative interference intensity of the other becomes also smaller cannot be maintained, in the same manner as the case of the combination of the waveforms shown in FIGS. 9(a) and 9(b).

In this case, there is only a slight difference between a value obtained by multiplying each relative interference intensity of the waveforms shown in FIGS. 9(a) and 9(b) and summing the obtained products for each λ, and a value obtained by multiplying each relative interference intensity of the waveforms shown in FIGS. 9(a) and 9(c) for each wavelength λ and summing obtained products for each λ. Accordingly, there is only a slight difference between relative interference intensities even though there is unevenness in the thickness.

As described above, there is only a slight difference in the total sum of the products of relative interference intensities for each λ between the combination of the waveforms shown-in FIGS. 9(a) and 9(b) and the combination of the waveforms shown in FIGS. 9(a) and 9(c). However, there is a difference in the products is of relative interference intensities for each λ. Accordingly, the discussion made with respect to FIG. 9 is not applicable when a single color light without having a width in the wavelength is used. Namely, it is impossible to control the fluctuation of intensity of transmitting light when the light does not having a width in wavelength λ.

In Examples of FIGS. 2 to 7, explanation is made as to the relative interference intensity with respect to two glass substrates wherein the half value width of light is 15 nm.

In the following, explanation will be made as to a case of irradiating light whose half value width is 5 nm with respect to the peak luminance (a width of ±2.5 nm with respect to the wavelength at the peak luminance). As such light, light having a center wavelength of 612 nm, emitted from a fluorescent lamp, is assumed.

The relative interference intensity in a case that the thickness of the first glass substrate is changed from 500,000 nm to 500,420 nm in the same manner as in FIGS. 2 to 7, will be described.

Figure 10:
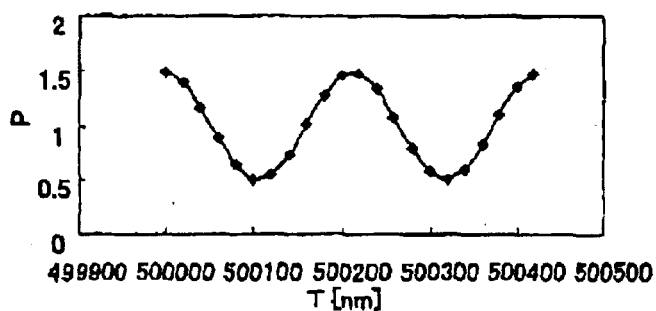
FIG. 10 is a graph showing a change of relative interference intensity caused by two glass substrates.

FIG. 10 shows a change of the relative interference intensity with a change of the thickness of the first glass substrate while the thickness of the second glass substrate is constant as 500,000 nm. As shown in FIG. 10, the relative interference intensity in the combination of two glass substrates varies within a range of from about 1.5 to about 0.5 according to a change of the thickness of the first glass substrate. For example, when the thickness of the first glass substrate is 500,000 nm, the relative interference intensity is about 1.5. However, when the thickness is 500,100 nm, the relative interference intensity is about 0.5. This shows that when unevenness of thickness takes place in either glass substrate, there occurs unevenness of intensity in the relative interference intensity.

Figure 11:
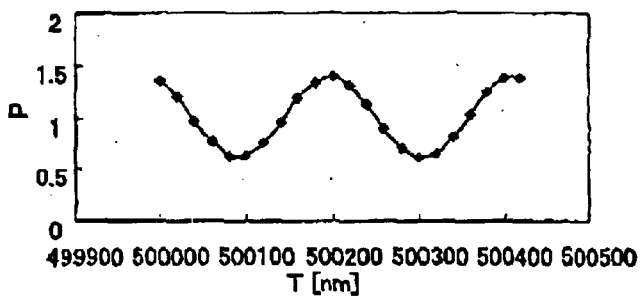
FIG. 11 is a graph showing a change of relative interference intensity caused by two glass substrates.

FIG. 11 is a graph showing a change of the relative interference intensity in a case that the thickness of the second glass substrate is determined to be 520,000 nm in the same manner as in FIG. 10. Even in the case of FIG. 11, the relative interference intensity by the combination of the two glass substrates varies with a change of the thickness of the first glass substrate. However, the difference between maximum and minimum values of the relative interference intensity is smaller than that in FIG. 10.

Figure 12:
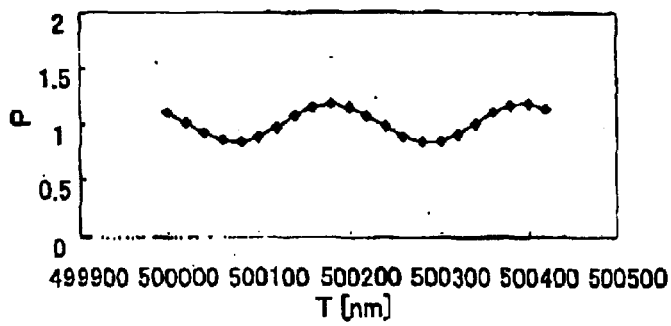
FIG. 12 is a graph showing a change of relative interference intensity caused by two glass substrates.

FIG. 12 is a graph showing a change of the relative interference intensity in a case that the thickness of the second glass substrate is determined to be 540,000 nm in the same manner as the cases shown in FIGS. 10 and 11. Even in the case of FIG. 10, the relative interference intensity by the combination of the second glass substrate varies with a change of the thickness of the first glass substrate. However, the difference between maximum and minimum values of the relative interference intensity is further smaller than that of the case shown in FIG. 11.

Figure 13:
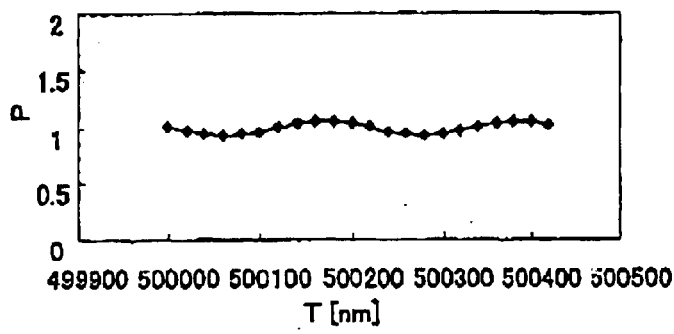
FIG. 13 is a graph showing a change of relative interference intensity caused by two glass substrates.
Figure 14:
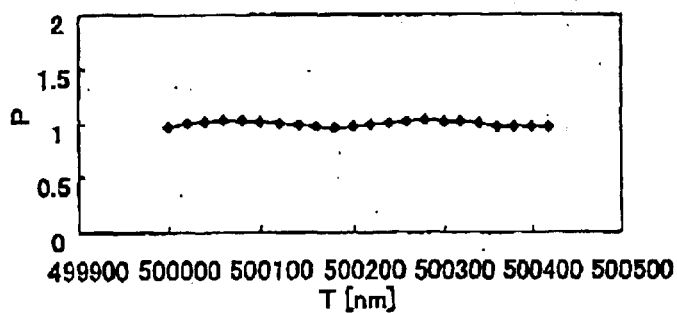
FIG. 14 is a graph showing a change of relative interference intensity caused by two glass substrates.
Figure 15:
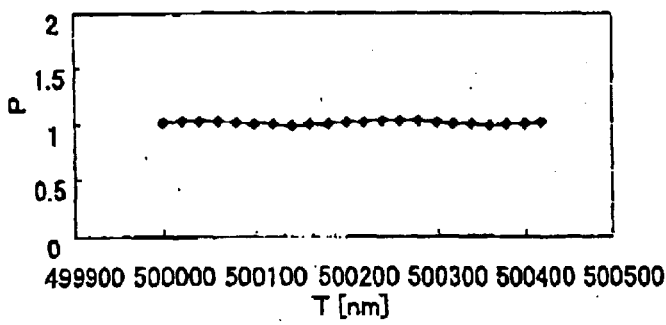
FIG. 15 is a graph showing a change of relative interference intensity caused by two glass substrates.

FIGS. 13, 14 and 15 are graphs showing relative interference intensities in cases that the thickness of the second glass substrate is determined to be 550,000 nm, 560,000 nm and 600,000 nm in the same manner as the cases shown in FIGS. 10 to 12. In the cases shown in FIGS. 13, 14 and 15, relative interference intensities do not show substantial changes even when the thickness of the first glass substrate is changed from 500,000 nm to 500,420 nm.

In view of the relative interference intensities shown in FIGS. 10 to 15, the same conclusion as the cases shown in FIGS. 2 to 7 can be derived. Namely, when the difference of thickness between adjacent glass substrates is smaller than 50,000 nm (0.05 mm) and if there is unevenness of thickness in a glass substrate, the conclusion that the relative interference intensities also change, is derived. Further, when the difference of thickness between adjacent glass substrates is at least 50,000 nm (0.05 mm), the conclusion that the relative interference intensities do not show substantial change is derived even though there is unevenness of thickness in a glass substrate. Further, as described before, when light without having no width in its wavelength λ is used, it is impossible to suppress the fluctuation of the relative interference intensities. However, it is understood that from FIGS. 10 to 15 that the fluctuation of the relative interference intensities can be suppressed when the half value width of light is to be at least 5 nm and the difference of thickness between adjacent glass substrates is to be at least 0.05 mm. In the liquid crystal display device shown in FIG. 1, the backlight 31 irradiating light whose half value width of at least 5 nm is used, and the difference of thickness between the glass substrate 2 at a front surface side of the displaying cell 1 and the glass substrate 28 at a rear surface side of the compensation cell 21 is at least 0.05 mm, is provided. Accordingly, the fluctuation in the relative interference intensities is slight and no line-shaped ununiformity of brightness occurs even though the thickness of the glass substrate 2 or the thickness of the glass substrate 28 is uneven.

Relative interference intensities shown in FIGS. 2 to 15 are derived from simulation by optical calculation. Although a technique of simulation is used, it is possible to obtain relative interference intensities as the case using actual liquid crystal devices.

FIG. 1 shows the case that the glass substrate 2 at a front surface side of the displaying cell 1 is at least 0.05 mm thicker than the glass substrate 28 at a rear surface side of the compensation cell 21. However, either one of two adjacent glass substrates 2, 28 may be thickened. Accordingly, the thickness of the glass substrate 28 at a rear surface side of the compensation cell 21 may be at least 0.05 mm thicker than the thickness of the glass substrate 2 at a front surface side of the displaying cell 1.

In the preparation of the liquid crystal display device of the present invention, thicknesses of the glass substrates 2, 28 are determined so that there is a difference of thickness of at least 0.05 mm between the thickness of the glass substrate 2 of the displaying cell 1 at a side of compensation cell 21 and the thickness of the glass substrate 28 of the compensation cell 21 at a side of displaying cell 1, and the glass substrates 2, 28 are prepared according to such determination. In this case, the glass substrates 2, 28 may have a certain degree of unevenness of thickness, such unevenness being resulted usually in the preparation of glass substrates. The displaying cell 1 is prepared by using the glass substrate 2. Similarly, the compensation cell 21 is prepared by using the glass substrate 28. In this case, the direction of twisting in the state of twisted alignment of the displaying cell 1 is opposite to that of the compensation cell 21.

Then, the first polarizing plate 32 is disposed at a rear surface side of the displaying cell 1, and the second polarizing plate 33 is disposed at a front surface side of the compensation cell 21. In a state that the displaying cell 1 and the compensation cell 21 are arranged adjacent to each other, the polarization axis of the first polarizing plate 32 should be perpendicular to the polarization axis of the second polarizing plate 33. Further, it is preferable that an angle of 45° is formed between the direction of polarization axis of the first polarizing plate 32 and the direction of alignment in the liquid crystal layer 5 of the displaying cell at a side of glass substrate 8 (a rear surface side), and an angle of 45° is formed between the direction of polarization axis of the second polarizing plate 33 and the direction of alignment in the liquid crystal layer 25 of the compensation cell 21 at a side of glass substrate 22 (a front surface side). Further, the displaying cell 1 and the compensation cell 21 are arranged so that directions of alignment of liquid crystal molecules at sides of adjacent glass substrates are perpendicular to each other. Further, a backlight for irradiating light whose half value width with respect to the peak luminance is at least 5 nm is disposed at a rear surface side of the first polarizing plate 32 in the displaying cell 1.

Although the twist angle and the birefringence value of liquid crystal in the displaying cell 1 are preferably made equal to those of the compensation cell 21, errors may take place in the preparation of them. Further, errors may take place in retardation values of the compensation cell 21 and the displaying cell 1 as long as the retardation value of the compensation cell 21 is not more than the retardation value of the displaying cell 1, specifically, the retardation value of the compensation cell 21 is in a range of from 80% to 100% of that of the displaying cell 1.

Similarly, even in the determination of angles, directions of alignment etc., errors may take place. For example, in a case that the first polarizing plate 32 and the second polarizing plate 33 are arranged so that their polarization axes are perpendicular, errors may take place. Such errors are permissible if the angle formed by their axes is not more than 5°. Further, errors may take place when the displaying cell 1 and the compensation cell 21 are arranged so that directions of alignment of liquid crystal molecules at sides of adjacent glass substrates are perpendicular to each other. Such errors are permissible if the angle formed by directions of alignment is not more than 5°. Further, errors may take place even when the displaying cell 1 and the compensation cell 21 are arranged so that the direction of the polarization axis of the first polarizing plate 32 and the direction of alignment in the liquid crystal layer 5 of the displaying cell 1 at a side of glass substrate 8 (a rear surface side) provide an angle of 45°, and the direction of the polarization axis of the second polarizing plate 33 and the direction of alignment in the liquid crystal layer 25 of the compensation cell 21 at a side of glass substrate 22 (a front surface side) provide an angle of 45°. Such errors are permissible if the angle formed by the direction of alignment and the polarization axis is from 40° to 50°.

FIG. 1 shows an embodiment that the glass substrate 2 at a front surface side (a side of compensation cell) of the displaying cell 1 is produced as a single glass sheet whose thickness is at least 0.05 mm thicker than the thickness of the glass substrate 28 at a rear surface side (at a side of the displaying cell) of the compensation cell 21. A substrate formed by bonding (optically adhering) a transparent sheet (a second transparent sheet) having a thickness of at least 0.05 mm to a glass sheet (a first transparent sheet) having the same thickness as the glass substrate 28 (the glass sheet) at a rear surface side of the compensation cell 21, may be used as the glass substrate 2 at a front surface side of the displaying cell 1. Similarly, a substrate formed by bonding a transparent sheet having a thickness of at least 0.05 mm to a glass sheet having the same thickness as the glass substrate 2 (glass sheet) at a front surface side of the displaying cell 1, may be used as the glass substrate 28 at a rear surface side of the compensation cell 21. In this case, the glass substrate 28 of the compensation cell 21 is at least 0.05 mm thicker than the glass substrate 2 of the displaying cell 1. The thickness of the glass sheet to be attached with the transparent sheet is equal to the thickness of the glass substrate 2 (or the glass substrate 28). In this case, however, errors may take place in the preparation.

Although it is preferable that refractive indices of glass sheets used for the glass substrates 2, 28 and transparent sheets to be bonded to the glass sheets are equal, they may be different. Even when the refractive indices are different from each other, the occurrence of a line-shaped ununiformity of brightness can be prevented when for instance, indices of the glass sheets and the transparent sheets are in a range of from 1.34 to 1.59. Table 1 shows the refractive index of each transparent substrate.

TABLE 1

| Material | Refractive index |
|---|---|
| Glass | 1.52 |
| Cytop | 1.34 |
| Polycarbonate (PC) | 1.59 |
| Polymethyl methacrylate (PMMA) | 1.49 |
| Polystyrene (PS) | 1.59 |

As shown in Table 1, the refractive index of glass is 1.52. Refractive index of cytop, polycarbonate (PC), polymethyl methacrylate (PMMA) and polystyrene (PS) are in a range of from 1.34 to 1.59. The cytop is a trademark registered in Japan of a fluorine type transparent resin manufactured by Asahi Class Company, Limited. The occurrence of a line-shaped ununiformity of brightness can be prevented even when a transparent sheet having a thickness of at least 0.05 mm made of a material having a refractive index of from 1.34 to 1.59 as shown in Table 1 is bonded to a glass sheet having a refractive index of 1.52. Further, the transparent sheet is not always necessary to have a refractive index of from 1.34 to 1.59. Further, the transparent sheet may be a transparent material exemplified in Table 1, instead of the glass sheet.

Description will be made as to how the liquid crystal display device of the present invention is used. The liquid crystal display device of the present invention can be used as, for example, a displaying portion of an instrument panel or a center panel of a vehicle. Further, it can be used as a displaying portion of a meter panel of an automatic two-wheeled vehicle or the like. Further, it may be used as an in-vehicle liquid crystal display device mounted on a vehicle or a liquid crystal display device for presenting information in public facilities or the like. For example, it may be used as a displaying panel for presenting various kinds of information instead of an advertising board, or as a guide panel for presenting various kinds of information to passengers in a train.

The quality of display of D-STN mode is influenced little by temperature. Accordingly, the liquid crystal display device of the present invention is in particular suitable for applications requiring a wide width of change of environmental temperature, such as applications to a vehicle, an outdoor equipment and so on.

In the present invention, the fluctuation of the relative interference intensity is suppressed by providing a difference of at least 0.05 mm between the thickness of the glass substrate 2 of the displaying cell 1 and the thickness of the glass substrate 28 of the compensation cell. Even in a case that the thickness of the glass substrate 2 at a front surface side of the displaying cell 1 is made equal to the thickness of the glass substrate 28 at a rear surface side of the compensation cell 21, a good quality of display without a line-shaped ununiformity of brightness can be realized by suppressing unevenness in the thickness. As understood from FIGS. 2 to 4 and FIGS. 10 to 12, periods of the fluctuation of the relative interference intensities are 200 nm (0.2 μm). Even in a case that the thickness of the glass substrate 2 at a front surface side of the displaying cell 1 is made equal to the thickness of the glass substrate 28 at a rear surface side of the compensation cell 21, a good quality of display without a line-shaped ununiformity of brightness can be realized if the glass substrates 2, 28 are prepared so that a difference between the thickest portion and the thinnest portion of the glass substrates is not more than the period of fluctuation (0.2 μm) of the relative interference intensity.

In the following, description will be made as to the reason with reference to FIG. 2, as an example.

FIG. 2 shows a change of the relative interference intensity in a case that the thickness of the second glass substrate is 500,000 nm and the thickness of the first glass substrate is changed from 500,000 nm. By changing the thickness of the first glass substrate from 500,000 nm to 500,100 nm, the relative interference intensity is changed from about 1.5 to about 0.5. However, in only providing a change of thickness of 100 nm, a state that a portion of low relative interference intensity is sandwiched between portions of high relative interference cannot be obtained. Accordingly, even though the relative interference intensity is changed largely from about 1.5 to about 0.5, the portion of low relative interference intensity is not conspicuous and it is difficult that the portion is recognized as a line-shaped ununiformity of brightness. When the thickness of the first glass substrate is further increased to 500,200 nm, the relative interference intensity is again returned to about 1.5. In this case, the portion of low relative interference intensity is sandwiched between portions of high relative interference intensity so that the portion of low relative interference intensity is conspicuous and it is recognized as a line-shaped ununiformity of brightness. Further, a difference of thickness between the thickest portion and the thinnest portion is not more than the period of fluctuation (0.2 μm) of the relative interference intensity, there is no possibility that a portion of low (or high) relative interference intensity is sandwiched between portions of high (or low) relative interference intensity. Accordingly, even when thicknesses of the glass substrates 2, 28 adjacent to each other in the displaying cell 1 and the compensation cell 21 are made equal, the occurrence of a line-shaped ununiformity of brightness can be prevented if the glass substrates 2, 28 are prepared so that a difference of thickness between the thickest portion and the thinnest portion is not more than 0.2 μm.

Figure 21:
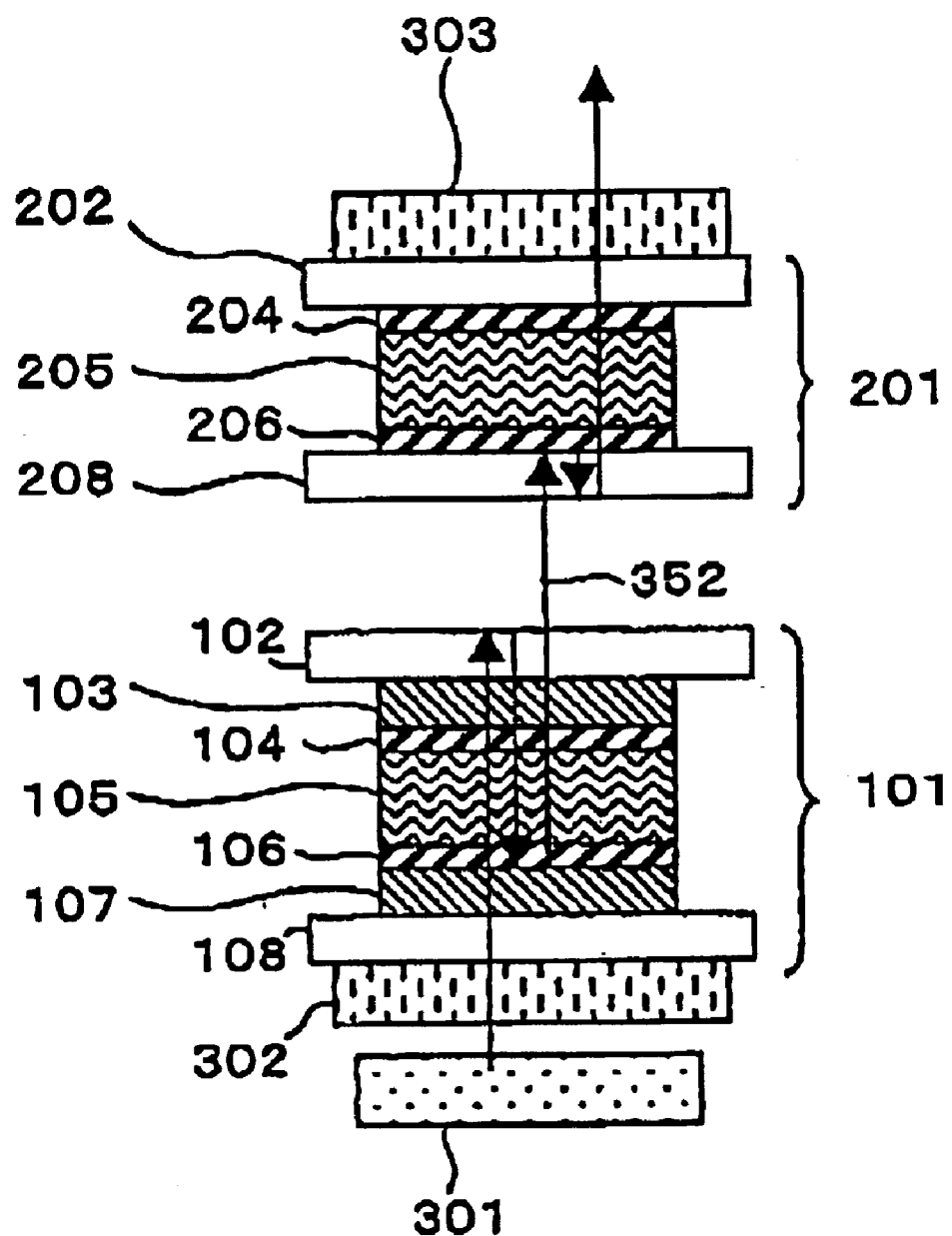
FIG. 21 is a diagram showing a cause of leakage of light.

With reference to FIG. 21, the cause of leakage of light when a dark appearance is to be displayed, has been described. However, another cause of leakage of light can be considered. Such phenomenon will be described with reference to FIG. 22.

Coherence length is in inverse proportional to the relative linewidth $\Delta\lambda/\lambda$ of the light, which means it is increasing with decreasing linewidth. Roughly, coherence length is the same multiple of the wavelength, as wavelength is a multiple of linewidth.

Typical red LED yields $\Delta\lambda/\lambda$ approx. 60 nm/600 nm=$\frac{1}{10}$, resulting in a coherence length of 10×λ, approx. 6000 nm=6 μm.

Figure 22:
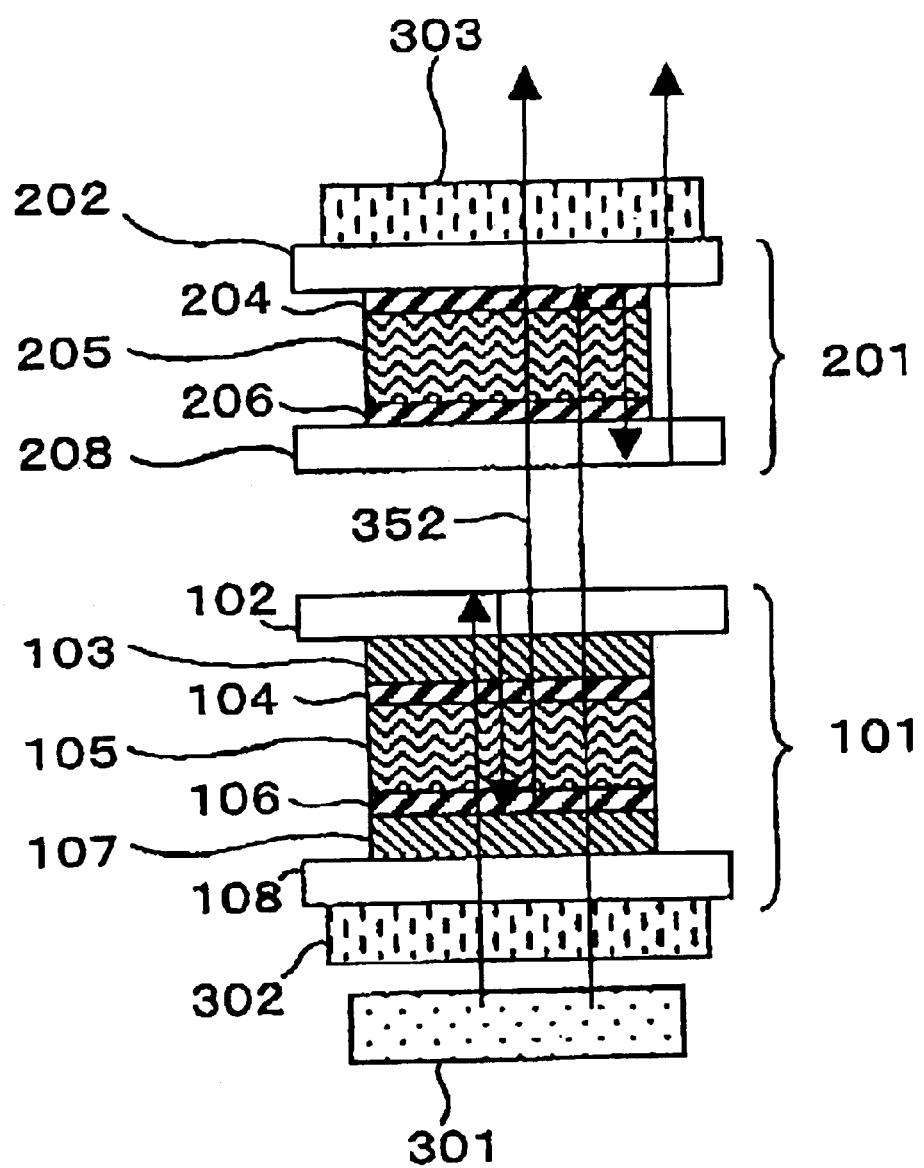
FIG. 22 is a diagram showing another cause of leakage of light.

In FIG. 22, interference is strong, if 2× thickness differences between glass 102 and 208 is less than the coherence length of approx. 6 μm. Interference gradually disappears, if thickness difference exceeds the coherence length. Practical thickness difference will be a multiple of this, therefore total avoidance of the interference is possible.

FIG. 22 shows a pair of paths, which we consider to be significant for the effect in DSTN.

The first path includes 1×cell 101+2×LC layer 105+2× alignment film 106+2×alignment film 104+2×transparent electrode 103+2×glass 102+1×cell 201.

The second path includes 1×cell 101+1×cell 201+2×LC layer 205+2×glass 208+2×alignment film 204+2×alignment film 206.

The path difference is 2×glass 102−2×glass 208 (LC layer difference is neglectable).

The number of internal reflections in each path is 2. If we calculate the reflection coefficient to be in the range of 5%, the relative intensity is 0.25% of the main light path. Any bigger number of internal reflections along the light path will strongly reduce the relative intensity further.

In the search for other significant "parasitic" light paths (which means, they are caused by internal reflections), we can exclude all, which have an equal number of paths through each LC layer. These will be blocked by the ordinary compensation effect of DSTN. We can further exclude all multiple paths through the polarizers. In addition, almost no reflection is caused by the interface of glass to polarizer we neglect the influence of ITO and other coating thicknesses of the internal layers in both cells and especially the different number and kind of coatings in cell 101 compared to cell 201.

This finally reduces the options for "effective" parasitic light paths to the one, which we mentioned above.

Now, the present invention will be described in detail with reference to Examples. However, it should be understood that the present invention is by no means restricted by such specific Examples.

EXAMPLE 1

A displaying cell was prepared in a manner as follows. A transparent electrode is disposed on each of two glass substrates of 0.7 mm thick, and an alignment film was formed on each of the transparent electrodes. A rubbing treatment was conducted to alignment films. In the rubbing treatment, the direction of rubbing was determined so as to form a twist angle of 180° in a state that the two glass substrates were combined by interposing liquid crystal therebetween. After the rubbing, the glass substrates were piled up so that the transparent electrodes each having the alignment film oppose to each other and liquid crystal was injected between the glass substrates in a shield state. As the liquid crystal, a commercially available liquid crystal ("ZLI4431": Δn=0.1643 manufactured by Merck) was used. The cell gap was 6 μm and Δn·d was 0.986 μm.

A compensation cell was prepared in a manner as follows. An alignment film was formed on each of two glass substrates of 0.55 mm thick, and a rubbing treatment was conducted to alignment films. In the rubbing treatment, the direction of rubbing was determined so as to form a twist angle of 180° in the same manner as in the displaying cell. After the rubbing, the glass substrates were piled up so that the alignment films oppose to each other, and liquid crystal was injected between the glass substrates in a shield state. The liquid crystal used was "ZLI4431" manufactured by Merck in the same manner as in the displaying cell. The cell gap of the compensation cell was 6 μm and Δn·d was 0.986 μm. However, in the compensation cell, the direction of twisting of liquid crystal molecules was opposite to that of the displaying cell.

Then, polarizing plates were bonded to the glass substrate to be located at a rear surface side of the displaying cell and the glass substrate to be located at a front surface side of the compensation cell, and the displaying cell and the compensation cell were arranged so that their surfaces on which the polarizing plates were not bonded, were opposed to each other. The polarizing plate was bonded to the displaying cell so that the direction of polarization axis of the polarizing plate and the direction of alignment in the liquid crystal layer of the displaying cell at a side of rear glass substrate form an angle of 45°. The polarizing plate was bonded to the compensation cell so that the direction of polarization axis of the polarizing plate and the direction of alignment in the liquid crystal layer of the compensation cell at a side of front glass substrate form an angle of 45°. Further, the displaying cell and the compensation cell were arranged so that directions of alignment of liquid crystal molecules at sides of adjacent glass substrates were perpendicular to each other, and directions of polarization axes of the two polarizing plates are perpendicular to each other. The thickness of each of the glass substrates of the displaying cell was 0.7 mm, and the thickness of each of the glass substrates of the compensation cell was 0.55 mm. Accordingly, the difference of thickness between the adjacent glass substrates in the displaying cell and the compensation cell is 0.15 mm which is larger than 0.05 mm.

Figure 16:
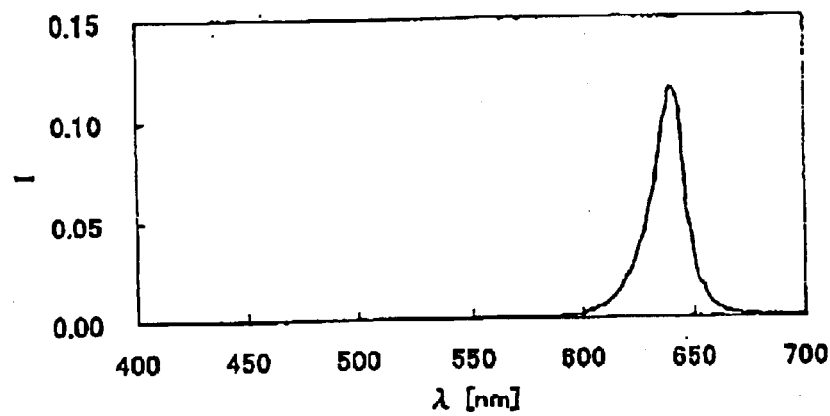
FIG. 16 is a graph showing the spectral luminance of the backlight used in Examples.

A backlight was disposed at a rear surface of the polarizing plate bonded to the displaying cell. LED was used as the backlight. FIG. 16 shows the spectral characteristics of the backlight used in this Example wherein the abscissa λ represents the wavelength and the ordinate I represents the luminance of light. The half value width in the spectral characteristics shown in FIG. 16 is 5 nm or more.

When no voltage was applied to the liquid crystal layer of the displaying cell, a display of good dark appearance was obtained without generating a line-shaped ununiformity of brightness.

COMPARATIVE EXAMPLE

A liquid crystal display device was prepared in the same manner as Example 1 except that glass substrates of 0.55 mm thick were used for the glass substrates of the displaying cell. Since the thickness of each glass substrate of the compensation cell is 0.55 mm, the difference of thickness between adjacent glass substrates in the displaying cell and the compensation cell is smaller than 0.05 mm. In this liquid crystal display device, ununiformity of display was found in the picture screen in a state that no voltage was applied to the liquid crystal layer of the displaying cell, and a good quality of display could not be obtained.

EXAMPLE 2

Glass substrates of 0.55 mm thick were used for the glass substrates of the displaying cell, and glass substrates of 0.5 mm thick were used as the glass substrates of the compensation cell. Then, a liquid crystal display device was prepared in the same manner as Example 1. The difference of thickness between adjacent glass substrates in the displaying cell and the compensation cell is 0.05 mm. A display of good dark appearance was obtained without generating a line-shaped ununiformity of brightness in a case that no voltage was applied to the liquid crystal layer of the displaying cell.

EXAMPLE 3

A glass substrate of 0.55 mm thick was used as the glass substrate at a front surface side of the displaying cell, and a glass substrate of 0.5 mm thick was used as the glass substrate at a rear surface side of the displaying cell. Further, glass substrates of 0.5 mm thick were used for the glass substrates of the compensation cell. Then, a liquid crystal display device was prepared in the same manner as Example 1. The difference of thickness between adjacent glass substrates in the displaying cell and the compensation cell is 0.05 mm. A display of good dark appearance could be obtained without generating a line-shaped ununiformity of brightness in a case that no voltage was applied to the liquid crystal layer of the displaying cell.

A liquid crystal display device was prepared in the same manner as comparative Example 1 except that glass substrates of 0.55 mm thick were used for the glass substrates of the displaying cell and the glass substrates of the compensation cell. Namely, the liquid crystal display device was prepared so that thicknesses of adjacent glass substrates of the displaying cell and the compensation cell were equal. In this case, however, polishing was conducted to the adjacent glass substrates in the displaying cell and the compensation cell so that the difference between the thickest portion and the thinnest portion was 0.2 μm or less. A display of good dark appearance could be obtained without generating a line-shaped ununiformity of brightness in a case that no voltage was applied to the liquid crystal layer of the displaying cell, unlike the case of Comparative Example 1.

In the following, description will be made as to an inspection method for a transparent substrate wherein a change of the relative interference intensity of two transparent substrates is utilized.

Assuming that two glass substrates (transparent substrates) are arranged adjacent to each other, such as the glass substrates 2, 28 as shown in FIG. 1, wherein either one of the glass substrates has no distribution of thickness, namely, it has no unevenness of thickness, and the other has a certain distribution of thickness, namely, it has a thick portion and a thin portion. When the thickness of the glass substrate is changed 0.1 μm (a is half of the period of fluctuation of the relative interference intensity), there appears a change in the relative interference intensity from a high state to a low state. Namely, the color of interference light changes from a dark state to a thin state. When the thickness is changed 0.2 μm (i.e., the period of fluctuation of the relative interference intensity), the relative interference intensity is changes from a high (dark) state to a low (thin) state and successively to be a high (dark) state, whereby such change is recognized as a single line-shaped ununiformity of brightness. The inspection method for a transparent substrate according to the present invention is a method utilizing this.

When a distribution of thickness is to be inspected, a first glass substrate having a predetermined thickness and a second glass substrate to be inspected are arranged adjacent to each other, and the presence or absence of a line-shaped ununiformity of brightness (interference fringes) is confirmed. The difference of thickness in average between the first glass substrate and the second glass substrate should be 50 µm or less. The two glass substrates are arranged so that they are adjacent to each other and light passes through each plane of the two glass substrates. For example, they are arranged so that planes of the glass substrates are opposed to each other. In this case, a substrate gap of at least 0.1 mm should be provided between the first glass substrate and the second glass substrate. As the first glass substrate, a very flat substrate without having any deviation of thickness (without having a distribution of thickness) is used. The second glass substrate to be inspected should be produced to have the same thickness as the first glass substrate. Namely, the second glass substrate has substantially the same thickness as the first glass substrate while it may have a distribution of thickness.

After the two glass substrates have been arranged in the above-mentioned manner, a distribution of the interference intensity of light passing through the two glass substrates is observed. The distribution of interference intensity is observed as an interference fringe(s) (a line-shaped ununiformity of brightness). The interference fringe(s) is different from Newton ring(s).

Figures 17A, 17B, 17C:
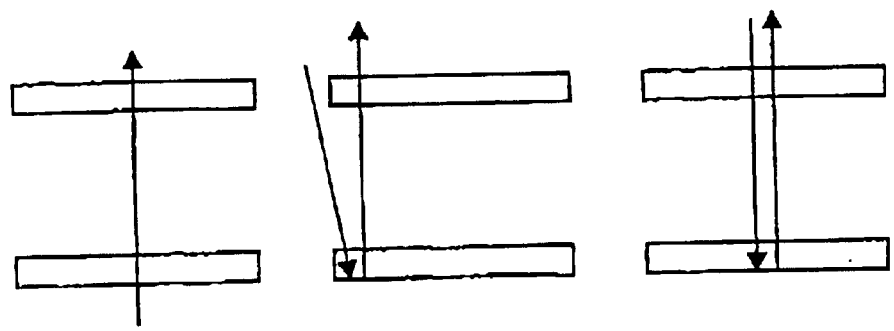
FIG. 17 is a diagram showing an example of the path of light in the inspection method according to the present invention.

FIG. 17 is a diagram showing Examples of path of light passing through two glass substrates, wherein FIG. 17(a) shows a path of light propagating linearly in the two glass substrates, FIG. 17(b) shows a path of light which enters into the glass substrate located at an opposite side of an observer; reflects on a rear surface of the glass substrate; comes out again the glass substrate at a opposite side of the observer, and passes through the glass substrate located at a side of the observer, and FIG. 17(c) shows a path of light which passes through the glass substrate located at a side of the observer to enter into the glass substrate located at an opposite side of the observer; reflects on the surface of the glass substrate, and passes through again the glass substrate at a side of the observer. In order to confirm the distribution of the interference intensity of light in this case, the distribution of the interference intensity of light tracing paths as shown in FIGS. 17(a) to 17(c) should be observed, for example.

In the inspection method of the present invention, a light source for irradiating light whose half value width with respect to the peak luminance is at least 5 nm is prepared so as to let such light pass through the two glass substrates. It is preferable to use natural light for such light.

When the second glass substrate has no distribution of thickness and has a thickness completely equal to the thickness of the first glass substrate, no line-shaped ununiformity of brightness takes place. It the second glass substrate has a certain distribution of thickness and the difference of thickness between the two glass substrates approaches a degree capable of causing an optical interference, a line-shaped ununiformity of brightness (an interference fringe) is apt to take place due to the interference of light passing through the two glass substrates. When the difference of thickness reaches about 0.2 µm, a single line-shaped ununiformity of brightness is observed. When the difference of thickness between the two glass substrates is further increased, the number of lines in the line-shaped ununiformity of brightness will increase. For example, when the difference of thickness is expanded to 0.4 µm, two lines are observed in the line-shaped ununiformity of brightness. Further, there appears a single line in the line-shaped ununiformity of brightness every time the difference of thickness expands to about 0.2 µm. Accordingly, the inspection as to how much the difference of thickness expands can be done by observing the number of lines in the line-shaped ununi-formity of brightness. When no line is observed, the judgment that the distribution of thickness in the second glass substrate is less than 0.2 µm, can be made. Namely, the judgment that the difference between the thickest portion and the thinnest portion is less than 0.2 µm, can be made.

In the observation of a line or lines in the line-shaped ununiformity of brightness, the judgment that the thickness of the second glass substrate increases about 0.2 µm every time a single line is added, can be made. Accordingly, the maximum value in the change of thickness of the second glass substrate can be calculated approximately as a value obtained by multiplying the number of lines in the line-shaped ununiformity of brightness by 0.2 µm. For example, when 10 lines are observed, the judgment that the difference of thickness between the second glass substrate and the first glass substrate is about 2 µm at the maximum, can be made. Accordingly, the judgment that the difference of thickness between the thickest portion and the thinnest portion of the second glass substrate is about 2 µm at the maximum, can be made. The above-mentioned approximate calculation can be realized in only the case that there is a difference of thickness between two glass substrates and the thickness of the second glass substrate is gradually increased or decreased. In case that the thickness of the second glass substrate is repeatedly thick and thin, the value of the difference of thickness between the two glass substrates is smaller than a value obtained by multiplying the number of lines in the line-shaped ununiformity of brightness by 0.2 µm.

Plural kinds of first glass substrates should be prepared so as to meet thicknesses of glass substrates to be produced. For example, when a glass substrate of 0.55 mm thick is produced and inspected, a glass substrate of 0.55 mm thick without having any distribution of thickness should be prepared as the first glass substrate. When a glass substrate of 0.5 mm thick is produced and inspected, a glass substrate of 0.55 mm thick without having any distribution of thickness should be prepared as the first glass substrate.

The inspection method of the present invention allows inspection to the thickness of a substrate or the presence or absence of unevenness of thickness of a substrate used for a liquid crystal display device, an organic EL display device or various kinds of flat panel display. When various kinds of first substrates as reference are prepared, a highly precise inspection can easily be done. In this case, it is preferable that the thickness of the second transparent substrate is 30 µm or more in average. If the substrate is too thin, interference takes place by the substrate itself. It is further preferable that the thickness is 100 µm or more.

The observation of the line-shaped ununiformity of brightness may be by visual check by human eyes or automatic inspection using a CCD camera.

The first glass substrate is not necessarily a very flat substrate without a deviation of thickness if the state of distribution of thickness of it is known. For example, even when the glass substrate has a portion having a different thickness and if the state of that portion is known, the other portion having a constant thickness can be used for inspection.

Figure 18:
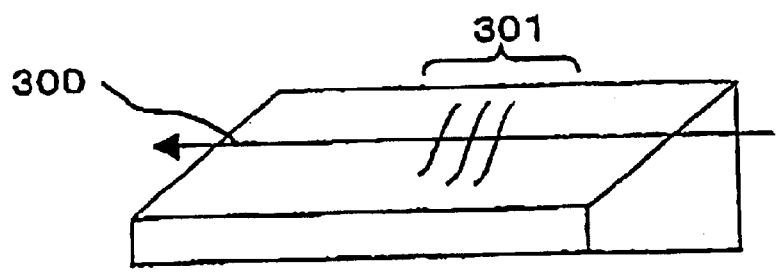
FIG. 18 is a diagram showing an example of a first glass substrate used for the inspection method of the present invention.
Figure 19:
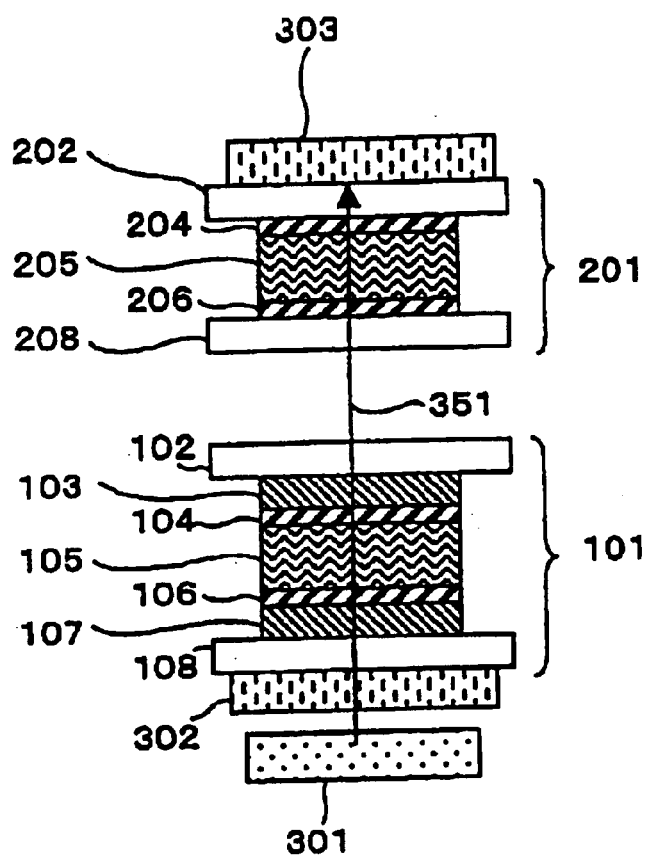
FIG. 19 is a diagrammatic cross-sectional view of a conventional liquid crystal display device.
Figure 20:
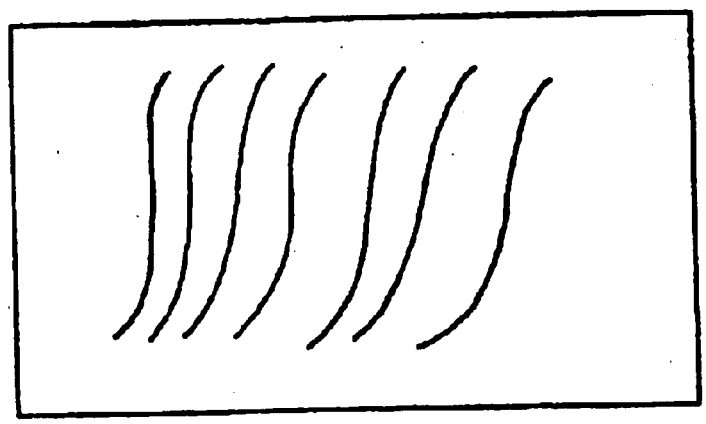
FIG. 20 is a diagram showing how a line-shaped ununiformity of brightness generates.

As shown in FIG. 18, even when a glass substrate whose thickness is changed in a wedge-like form is used as the first glass substrate, it is possible to confirm a change in the thickness of the second glass substrate by finding the number of lines in a line-shaped ununiformity of brightness 301 resulted in a direction perpendicular to the direction 300 along which the thickness is unchanged.

A substrate to be inspected is not limited to a substrate for a liquid crystal display device, an organic EL display device or various kinds of flat panel display. A glass substrate usable with another substrate in parallel may be an object to be inspected. For example, a glass substrate usable solely such as a cover glass for a solar cell may be an object to be inspected. Further, a transparent substrate other than glass (e.g., a plastic substrate) may be an object to be inspected.

According to the liquid crystal display device of the present invention, a display of good quality can be provided without generating a line-shaped ununiformity of brightness even when there is leakage of light in presenting a display of dark appearance. Further, according to the inspection method for a transparent substrate according to the present invention, unevenness of thickness in a substrate can easily be confirmed.

The entire disclosure of Japanese Patent Application No. 2002-126916 filed on Apr. 26, 2002 including specification, claims, drawings and summary is incorporated herein by reference in its entirety.

What is claimed is:

1. A liquid crystal display device comprising:

a displaying liquid crystal cell having a liquid crystal layer sandwiched by a pair of transparent substrates with transparent electrodes so as to maintain a state of twisted alignment when a voltage applied to the liquid crystal layer is not more than the threshold voltage, a compensation cell having a liquid crystal layer sandwiched by a pair of transparent substrates so as to maintain a state of twisted alignment in which the direction of twisting is opposite to that in the displaying liquid crystal cell and the twist angle is substantially the same as that of the displaying liquid crystal, the compensation cell having substantially the same retardation value as the displaying liquid crystal cell, wherein the displaying liquid crystal cell and the compensation cell are arranged so that directions of alignment of liquid crystal molecules at sides of adjacent transparent substrates are substantially perpendicular to each other, and a pair of polarizing plates disposed to sandwich the displaying liquid crystal cell and the compensation cell so that their polarization axes are substantially perpendicular to each other, the liquid crystal display device being characterized in that:

a backlight is disposed to irradiate light whose half value width with respect to the peak luminance is at least 5 nm, and there is a difference of thickness of at least 0.05 mm between the thickness of the transparent substrate of the displaying liquid crystal cell at a side of compensation cell and the thickness of the transparent substrate of the compensation cell at a side of displaying liquid crystal cell.

2. The liquid crystal display device according to claim 1, wherein the liquid crystal display device is an in-vehicle liquid crystal display device mounted on a vehicle or a displaying liquid crystal device for presenting information to public.

3. The liquid crystal display device according to claim 1, wherein there is an air spare of at least 75 μm between the displaying liquid crystal cell and the compensation cell.

4. A method of making a liquid crystal display device, the method comprising sandwiching a liquid crystal layer between a pair of transparent substrates with transparent electrodes so as to form a displaying liquid crystal cell;

sandwiching a liquid crystal layer between a pair of transparent substrates so as to form a compensation cell; and producing the liquid crystal display device of claim 1.

5. A liquid display device comprising:

a displaying liquid crystal cell having a liquid crystal layer sandwiched by a pair of transparent substrates with transparent electrodes so as to maintain a state of twisted alignment when a voltage applied to the liquid crystal layer is not more than the threshold voltage, a compensation cell having a liquid crystal layer sandwiched by a pair of transparent substrates so as to maintain a state of twisted alignment in which the direction of twisting is opposite to that in the displaying liquid crystal cell and the twist angle is substantially the same as that of the displaying liquid crystal cell, the compensation cell having substantially the same retardation value as the displaying liquid crystal, wherein the displaying liquid crystal cell and the compensation cell are arranged so that directions of alignment of liquid crystal molecules at sides of adjacent transparent substrates are substantially perpendicular to each other, and a pair of polarizing plates arranged to sandwich the displaying liquid crystal cell and the compensation cell so that their polarization axes are substantially perpendicular to each other, the liquid crystal display device being characterized in that:

a backlight is disposed to irradiate light whose half value width with respect to the peak luminance is at least 5 nm, and the transparent substrate of the displaying liquid crystal cell at a side of compensation cell and the transparent substrate of the compensation cell at a side of displaying liquid crystal cell are provided with first transparent sheets of substantially same thickness, and the first transparent sheet of either the transparent substrate of the displaying liquid crystal cell at a side of compensation cell or the transparent substrate of the compensation cell at a side of displaying liquid crystal cell is in optically close contact with a second transparent sheet having a thickness of at least 0.05 mm.

6. A method of making a liquid crystal display device, the method comprising sandwiching a liquid crystal layer between a pair of transparent substrates with transparent electrodes so as to form a displaying liquid crystal cell;

sandwiching a liquid crystal layer between a pair of transparent substrates so as to form a compensation cell; and producing the liquid crystal display device of claim 5.

* * * * *